United States Patent
Pessenhofer

(10) Patent No.: US 6,387,053 B1
(45) Date of Patent: May 14, 2002

(54) METHOD AND APPARATUS FOR DETERMINING AN INDICATOR WHICH IS DEPENDENT ON RESPIRATORY DATA

(75) Inventor: Herfried Pessenhofer, Graz (AT)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 09/576,958

(22) Filed: May 24, 2000

(30) Foreign Application Priority Data

May 25, 1999 (AT) ................................................ 932/99

(51) Int. Cl.⁷ ................................................ A61B 5/08
(52) U.S. Cl. ...................... 600/531; 600/529; 600/532
(58) Field of Search ................................ 600/529, 531, 600/532, 533, 538

(56) References Cited

U.S. PATENT DOCUMENTS

| | | | |
|---|---|---|---|
| 4,463,764 A | | 8/1984 | Anderson et al. |
| 4,724,845 A | * | 2/1988 | Callahan ............... 600/531 |
| 5,207,623 A | * | 5/1993 | Tkatshouck et al. ........ 600/538 |
| 5,297,558 A | | 3/1994 | Acorn et al. |
| 5,383,469 A | | 1/1995 | Vreman et al. |
| 5,448,998 A | * | 9/1995 | Ito et al. ..................... 600/531 |
| 5,533,513 A | | 7/1996 | Ueda et al. |
| 5,782,772 A | | 7/1998 | Stegmann |

OTHER PUBLICATIONS

H. Pessenhofer et al., "Untersuchungen zur Aussagefähigkeit des . . . E. A. Müller" in Eur. J. Appl. Physiol. 40, 255–264 (1979).

* cited by examiner

*Primary Examiner*—Kevin Shaver
*Assistant Examiner*—Navin Natnithithadha
(74) *Attorney, Agent, or Firm*—Dykema Gossett PLLC

(57) ABSTRACT

In a method for the determination of an indicator which depends on respiratory data and defines the transition from the aerobic to anaerobic metabolism of a person, with the person being subjected to a physical stress, the $O_2$ and $CO_2$ concentration is measured directly in the respiratory gas stream of the person or in a partial stream derived there from. The time course of the concentration values or discrete concentration values are measured within at least one respiration period and the indicator defining the aerobic-to-anaerobic transition is derived from the time course of the concentration values or from discrete concentration values using a mathematical model.

18 Claims, 3 Drawing Sheets

METHOD AND APPARATUS FOR DETERMINING AN INDICATOR WHICH IS DEPENDENT ON RESPIRATORY DATA

BACKGROUND OF THE INVENTION

The invention relates to a method for determining an indicator which is dependent on respiratory data and defines the transition from the aerobic to the anaerobic metabolism of a person, with said person being subjected to physical stress, as well as an apparatus to perform the method, The physical performance capacity of an organism constitutes an integrative and imprecisely described value which is to quantify the ability to tolerate physical stress. As a result of physical stress several subsystems of the organism are loaded in different forms and intensities depending on the respective state of training. The most important of said subsystems are, in addition to the neuromuscular systems for initiating the sequence of motions, the oxygen transport system (respiration, diffusion of the respiratory gases, oxygen binding to hemoglobin, cardiovascular system) and the metabolic system of the working skeletal muscles.

Since the metabolic system of the skeletal muscle constitutes the performance-limiting system in the healthy person, the muscular metabolism is given primary attention in exercise-resp. work physiology.

In order to perform physical activities it is necessary that the muscle is able to rely on a pool of adenosine triphosphate (ATP) as a direct source of energy (see FIG. 1). With the exception of short-time work for which only phosphate stores are used, two metabolic ways are available for its resynthesis which are used depending on the respective requirements concerning intensity of work and duration of work. The most important and energetically most favourable way is the aerobic metabolism in which the substrates glycogen and glucose and also free fatty acids are degraded into carbon dioxide and water, provided an adequate supply of oxygen via respiration and circulation.

The aerobic pathway, however, can only provide moderately high energy flow rates, therefore the second metabolic variant, the anaerobic pathway, is additionally activated for performance of higher work load intensities (also at the beginning of physical work). This mechanism of providing energy uses glycogen and glucose as a substrate, but supplies lactate as an end product. It is usually produced more rapidly than it can be degraded and therefore accumulates in the organism. At the same time hydrogen ions are produced, so that termination of the activities occurs by muscular exhaustion due to the local acidosis in connection with the rise in lactate.

Physical stress in which primarily the aerobic metabolic pathway is used is the ideal and desirable form of health training, e.g. endurance training, because an economisation of the cardiovascular system is achieved on the one hand and mobilization of metabolism and the lipocatabolism are promoted on the other hand.

In exercise physiology the idealized assumption as illustrated in FIG. 2 is frequently made that the energy needs (by taking into account the mechanical efficiency) as predetermined by the exercise protocol are covered by way of the biochemical energy liberation as long as the demanded strain is lower than the individually determined maximum strain. In the exercise protocol illustrated the total expenditure of energy increases according to an approximately quadratic function.

The maximum share to be covered via the aerobic metabolism is illustrated by a straight line whose slope depends on the maximum aerobic capacity of the test person (which among other things is a function of the state of training).

Once the total expenditure exceeds the maximum expenditure that can be provided aerobically, the differential share to the total expenditure must be provided by way of the anaerobic metabolism.

The time $T_{an}$, namely the moment of the transition from aerobic to anaerobic, in which the aerobic provision of energy is exceeded is stated (with a defined exercise protocol) in units of stress (e.g. watts).

When implemented practically, however, the transition from aerobic to anaerobic metabolism cannot be defined precisely by a moment or a stress value, so that frequently a transition area is defined at the lower limit (aerobic threshold) of which the change of the energetic metabolism begins and at the upper limit (anaerobic threshold) of which the same is completed.

Since the intensity of stress at which the organism switches from the energetically more favourable aerobic metabolism to the anaerobic metabolism depends on the respective state of training and thus on the physical work capacity, various indicators are defined within the scope of ergometric tests or performance tests which are based on various physiological indicators or variables of the involved subsystems of the organism and their changes as a consequence of standardized exercise protocols.

Depending on their assignment to the various subsystems the following indicators are known:
Lactate-oriented indicators
Heart-rate-oriented indicators
Indicators dependent on respiratory variables The lactate concentration in the blood is used as a biological variable in the case of lactate-oriented indicators. In order to obtain a numerical value in terms of physical work, the functional relation between lactate concentration and work load on the ergometer is determined empirically using a standardized protocol with stepwise increasing work load. The work load at two defined lactate concentrations, namely 2 mmol/l and 4 mmol/l is used as a characteristics for the physical performance capacity. The 2 mmol/l value is defined as the aerobic threshold and the 4 mmol/l value as the anaerobic threshold. The intermediate range is designated as aerobic-to-anaerobic transition.

Where heart-rate-oriented criteria are concerned, either absolute values of the heart rate (e.g. 60% of the maximum heart rate) or specifics of the time course of the heart rate (discontinuities or deflection points) in an increasing work load protocol are used as an indicator for the transition from the aerobic to the anaerobic metabolism. The best known example of this test method is the so-called CONCONI test.

Respiratory-oriented criteria are based on the physiological fact that when using the anaerobic metabolism in addition to lactate hydrogen ions are formed which lead to a metabolic acidosis. The hydrogen ions are buffered by the bicarbonate buffer-system of the blood, with $CO_2$ being liberated. It is expired via the respiratory system. Caused by respiratory control, a compensatory hyperventilation is initiated, so that carbon dioxide is expired more intensively. Therefore one frequently puts the oxygen consumption in relationship with the carbon dioxide output (e.g. by calculating the so-called "respiratory exchange ratio —RER") and tries this way to derive the indicators for the transition from the aerobic to the anaerobic metabolism.

The indicators used most frequently in performance diagnostics are the lactate-oriented ones, namely the so-called lactate thresholds. Their advantage is the ability to be determined precisely by measurements. Their disadvantage is the necessity to take blood from the hyperemisized ear lobe and the required instrumentation for the chemical analysis.

Heart-rate-oriented indicators are easy to be determined non-invasively. As a result of the indirect representation of muscular metabolism with respect to a cardiovascular variable, they show a lack of precision and reproducibility, however.

Respiratory-oriented indicators have the advantage of a direct relation to the muscular metabolism (metabolic acidosis). Their determination, however, relies on conventional methods of ergospirometry, and on extensive equipment.

DESCRIPTION OF THE PRIOR ART

From U.S. Pat. No. 5,297,558 for example an algorithm is known for the determination of an indicator for the "fat burning point". This point substantially corresponds to the aforementioned aerobic-to-anaerobic transition and is determined conventionally on the basis of respiratory variables. The so-called respiratory exchange ratio (RER) is determined by means of an ergospirometry system known from U.S. Pat. No. 4,463,764 on the basis of oxygen consumption (volume/time) and carbon dioxide output (volume/time). The heart rate at the work load intensity at which said RER exceeds the numerical value of 0.9 is used as an indicator value and percentage mark-ups and mark-downs on said heart rate value form the optimal intensity range (now stated on the basis of the heart rate) for the training. The disadvantageous aspect is the required determination of the respiratory flow (ventilation). Moreover, the determination of the respiratory flow is frequently subject to errors due to the required breathing masks and mouthpieces (leakage problems), with the use of tightly fitting masks and the breathing through mouthpieces generally being regarded as unpleasant.

From U.S. Pat. No. 5,782,772 A a method and an apparatus are further known for determining the individual anaerobic threshold, with the respiratory flow (ventilation) $V_E$, the carbon dioxide output $V_{CO2}$, and the oxygen consumption $V_{O2}$, being determined as primary variables. All aforementioned variables are so-called "flow variables" with the physical dimension of volume/time (unit: l/min, ml/min, etc.). The determination of these values necessitates in all cases a gas-tight breathing mask, with the disadvantages occurring as explained in connection with U.S. Pat. No. 4,463,764. The respective gas concentrations need to be measured to determine the carbon dioxide output and the oxygen consumption.

SUMMARY OF THE INVENTION

It is the goal of the present invention to provide a method and an apparatus to perform the method in order to enable a simple determination of the aerobic-to-anaerobic transition on the basis of respiratory criteria, with unpleasant circumstantial conditions being substantially avoided for the test person in the application of the method or apparatus.

This objective is achieved in accordance with the invention in such a way that the $O_2$ and $CO_2$ concentrations are measured directly in the person's respiratory gas stream or in a partial stream derived there from, with the time course of the concentration values being acquired within at least one period of respiration, and that the indicator defining the aerobic-to-anaerobic transition is derived by using a mathematical model from the time course of the concentration values.

As an alternative it is possible that discrete $O_2$ and $CO_2$ concentration values are measured at predetermined times (e.g. by using a thermistor probe) in the course of at least one respiration period, with the indicator defining the aerobic-to-anaerobic transition being derived from the discrete $O_2$ and $CO_2$ concentration values by using a mathematical model.

In contrast to the conventional determination of respiratory flow, reference is made exclusively to the time course or determination at certain points of the concentration values of oxygen and carbon dioxide in the course of at least one respiration period. An indicator value is calculated on the basis of these by using an empirical mathematical model (cf. FIGS. 5 and 6 for example) or one that is derived from physiological-medical basic information.

The indicator characterizing the transition from the aerobic to the anaerobic metabolism can be used as a guideline for controlling the intensity of training within the scope of stationary institutions such as fitness centers or individual outdoor training measures such as jogging for example. It can also be used for purposes of diagnosis of physical performance, namely to determine physical performance capacity. In the latter case it is necessary to measure the performance provided by the person subjected to a physical stress in addition to the concentration values in order to be able to assign the calculated indicator to a specific work load.

An apparatus in accordance with the invention for the determination of an indicator which defines the transition from the aerobic to anaerobic metabolism of a person is characterized in such a way that positionable sensors for the measurement of the $O_2$ and $CO_2$ concentration are positioned directly in the respiratory gas stream or a partial stream gained from the respiratory gas stream, which sensors are suitable for detecting the time course of the concentration values or discrete concentration values within at least one respiratory cycle. Measurement is thus performed either quasi-continuously or in form of discrete values (e.g. minimum or maximum values). Preferably, measurement can be performed directly in the respiratory gas stream, with the sensors being positioned on a fixing device similar to a hands-free kit in front of the mouth, or a partial stream can be gained from the respiratory gas stream by means of a mask- or funnel-like apparatus which rests loosely on the person's mouth and nose. In the latter case a device for drying the respiratory gases can be provided between the mask-like apparatus for gaining the partial stream and the sensors for measuring the $O_2$ and $CO_2$ concentration.

It is advantageous when the time course of the $O_2$ and $CO_2$ concentration is determined over several respiratory cycles under similar stress and the result is preferably stored in digitized form.

It is provided in a preferable embodiment of the invention that the final expiratory values for $O_2$ and $CO_2$ are calculated from the time course of the $O_2$ and $CO_2$ concentration values and are used for the derivation of the indicator.

It is provided further in accordance with the invention that the work load intensities and the heart rate of the person are measured in addition and are displayed as diagnostic values or used as control values, or that values are considered in the mathematical model which describe the mixing characteristics of the respiratory system, the compartmentalization of the muscular metabolism and the buffer system of the blood and/or the gas transport and signal characteristics of the measurement system.

In accordance with the invention it is also possible to use shape criteria of the expiratory part of the time course of the $O_2$ and $CO_2$ concentration values for determining the indicator. Representative is thus not only the calculated end expiratory concentration value, but also the shape of the time course (rise, discontinuities, etc.) in the expiratory phase.

BRIEF DESCRIPTION OF THE DRAWINGS

The invention will now explained in greater detail by reference to the enclosed drawings, wherein.

DETAILED DESCRIPTION OF THE PREFERRED EMBODIMENTS

Figure 1:
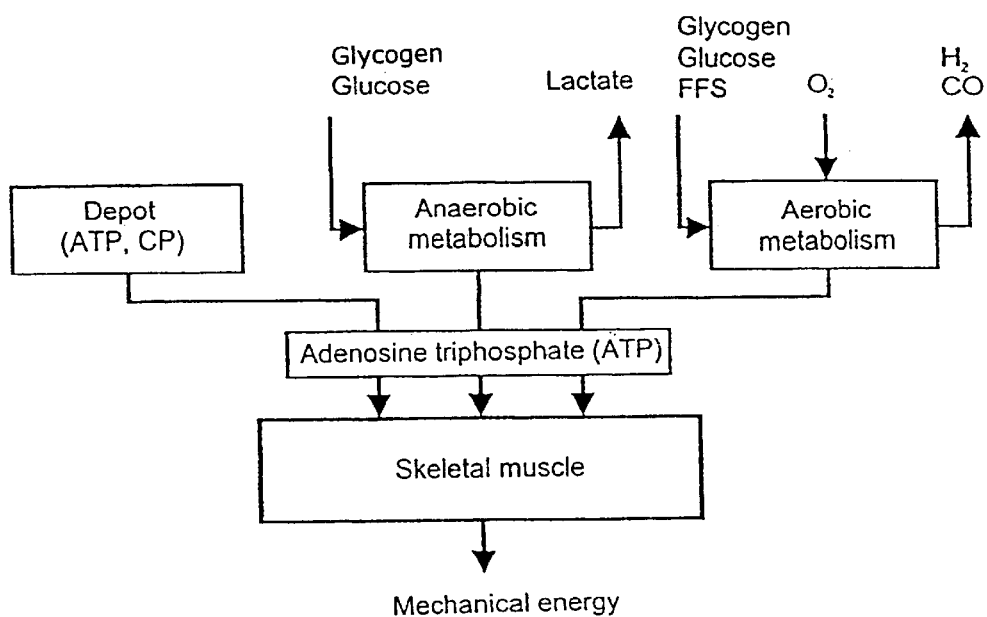
FIG. 1 shows a graphical illustration of the different metabolic pathways for the provision of metabolic energy.
Figure 2:
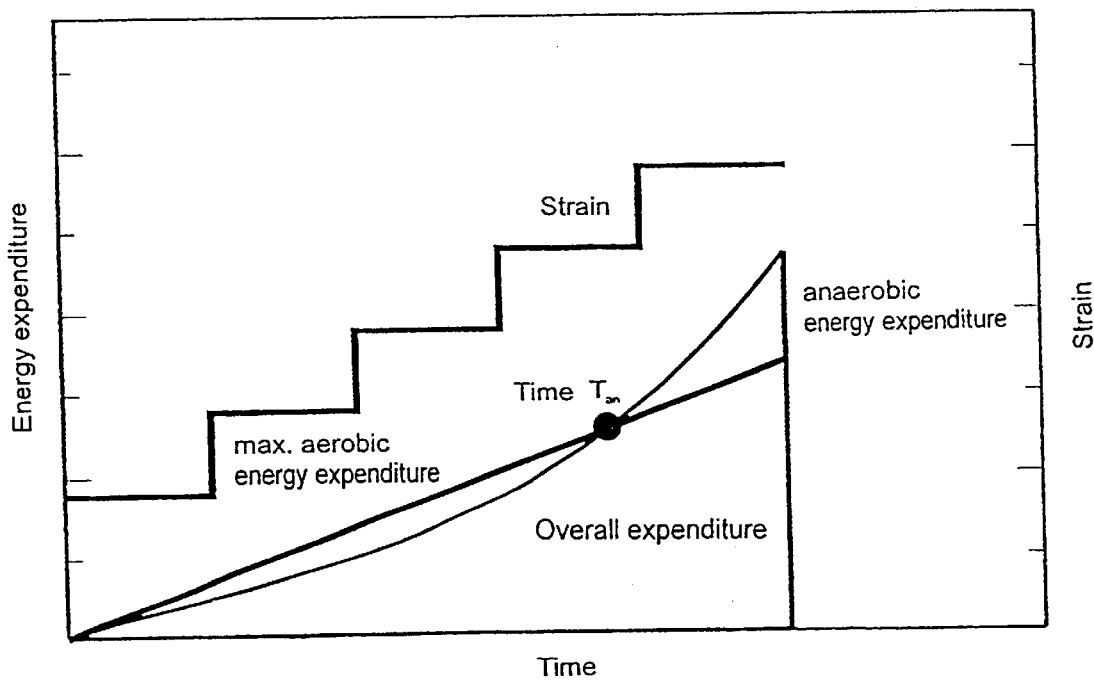
FIG. 2 shows the diagram of a work load protocol.

The problems as illustrated graphically in FIGS. 1 and 2 have already been discussed in detail above.

Figure 3:
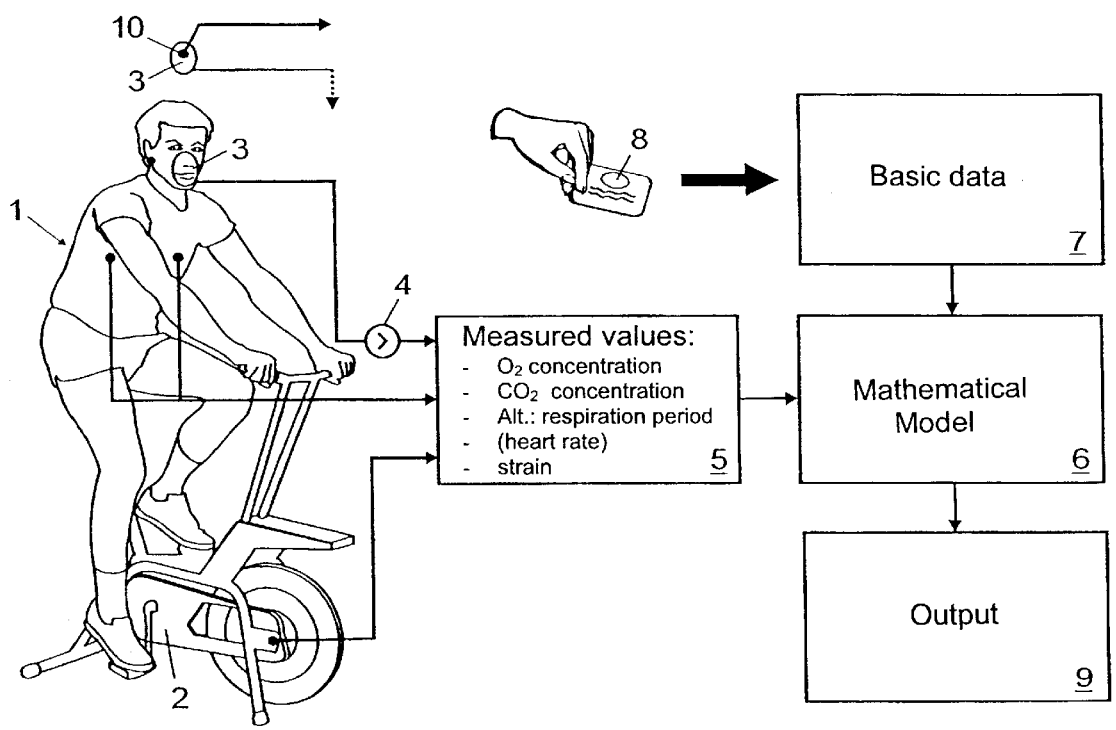
FIG. 3 shows the apparatus in accordance with the invention in a partial schematic view.
Figure 4:
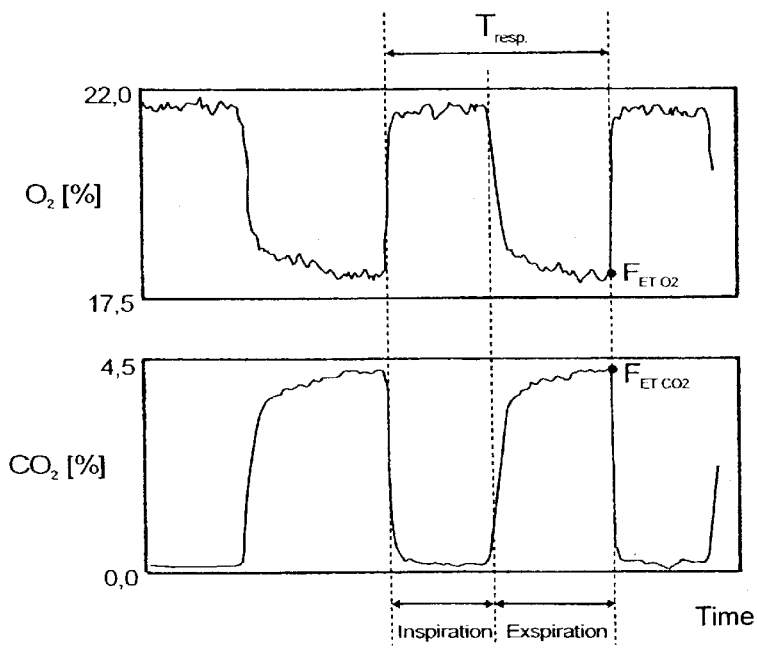
FIG. 4 shows the time course of the $O_2$ and $CO_2$ concentration values in the inspiration and expiratory phase of several respiration periods ($T_{resp}$)

FIG. 3 shows an apparatus in accordance with the invention for determining an indicator which depends on measured data and characterizes the transition from the aerobic to the anaerobic metabolism of a person 1. The person is subjected to physical stress, e.g. by a bicycle ergometer 2. The respiratory exchange of gas of the test person is detected by means of a loosely fitting mask-like apparatus 3 and a constant partial stream is drawn off by means of a pump 4. Following optional drying it is supplied to a measurement unit 5 with gas analyzers with a low response time for oxygen and carbon dioxide. Furthermore, measurement unit 5 is supplied with data on the current work load of the test person and the performance provided by the same and the test person's heart rate. The data are processed in a processor unit 6 on the basis of a mathematical model. Person-related basic data such as age, weight, height, sex and training condition of the test person can be entered through a further unit such as a magnetic card 8 for example. The calculated data are displayed in a display or output unit 9. Alternatively, a thermistor sensor 10 for the detection of the respiratory cycle can be provided in the mask-like apparatus 3 or directly in the test person's nose.

The apparatus in accordance with the invention can also be arranged as a portable mobile device which is carried along during training (e.g. jogging) or can be fastened to the body.

The time course of the $O_2$ and $CO_2$ concentrations are recorded over several respiration periods $T_{resp}$ (approx. 10 periods) and stored digitally. The end-expiratory values for $O_2$ and $CO_2$-concentrations are designated with $F_{ET02}$ and $F_{ET02}$.

Figure 5:
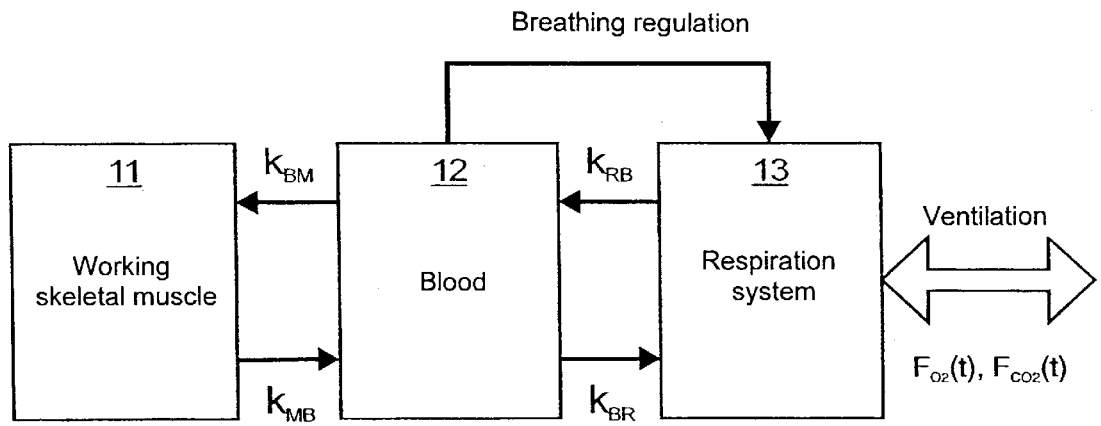
FIG. 5 shows the graphical illustration of a mathematical model for determining an indicator value, and FIG. 6 shoes the course of the respiratory etabolic indicator (RMI) as a function of physical stress.

Indictors for the status of the muscular metabolism are identified through a mathematical model from the stored time functions. This model can consist of three submodels (see FIG. 5) according to the compartmentalization of the involved physiological systems, namely the working skeletal muscle 11, the blood compartment 12 and the respiratory system 13. A functional connection between the production of hydrogen ions on the one hand and lactate production, work load, oxygen consumption, cardiac output and utilized substrates on the other hand is established in submodel 11. Submodel 12 represents a functional characterization of the bicarbonate buffer system of the blood and the $CO_2$ production as a result of the activities of this system. A functional connection between the gas concentration values in the blood and the time courses of the respiratory gas concentrations is established in submodel 13, with said formal approach including anthropometric data of the person (height, weight, age) as well as characteristics of the respiratory system (resistance, functional residual capacity, etc.) and the work load intensity. The effect of respiratory control on the $CO_2$ concentration curve in the respiratory gas stream is modeled through a non-linear functional approach. The overall model which is formulated in the form of a system of differential equations in conjunction with algebraic equations is identified on the basis of experimentally determined time courses for $O_2$ and $CO_2$ concentration as well as on the basis of the anthropometric data representing fixed parameters.

A criterion value is calculated on the basis of the identified model parameters which represents an image of the metabolic situation of the working skeletal muscle, represented by the production of lactate and hydrogen ions. This indicator also considers the different dynamics in the change of metabolic and respiratory variables.

Figure 6:
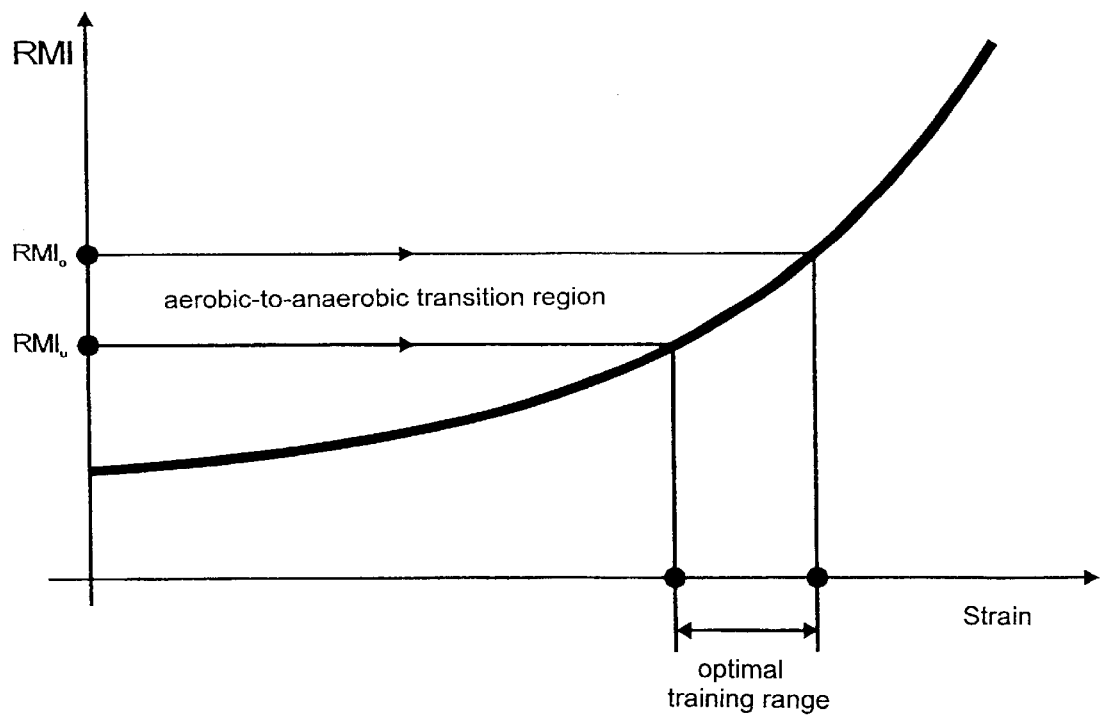

As is illustrated in FIG. 6, thresholds for the aerobic-to-anaerobic transition range can be defined according to empirical criteria (RMI, and RMI,) for the resulting respiratory-metabolic indicator (RMI) as a function of the stress.

The determined indicators can put in relationship with the work load intensity and the heart rate at the respective stress and can be used as a diagnostic information for the physical capacity of the respective test person and as a control value for endurance training.

I claim:

1. A method for determining an indicator which is dependent on respiratory data and defines a transition from an aerobic to an anaerobic metabolism of a person, with said person being subjected to a physical stress, wherein $O_2$ and $CO_2$ concentrations are measured directly in said person's respiratory gas stream, with the time course of said $O_2$ and $CO_2$ concentration values being acquired within at least one respiration period, and wherein said indicator defining said aerobic-to-anaerobic transition is derived by using a mathematical model from said time course of said $O_2$ and $CO_2$ concentration values.

2. A method according to claim 1, wherein said $O_2$ and $CO_2$ concentration values are measured in a partial stream derived from said person's respiratory gas stream.

3. A method according to claim 1, wherein said time course of said $O_2$ and $CO_2$ concentration is determined over several of said respiration periods under constant stress and the results are stored in a digitized form.

4. A method according to claim 1, wherein end-expiratory values for $O_2$ and $CO_2$ are calculated from said time course of said $O_2$ and $CO_2$ concentration values and are used to derivate said indicator.

5. A method according to claim 1, wherein the work load and the heart rate of said person are measured in addition and are displayed as diagnostic values or used as control values.

6. A method according to claim 1, wherein additional values are considered in said mathematical model which describe at last one feature of a group consisting of the mixing characteristics of said respiratory system, the compartmentalization of the muscular metabolism and the buffer system of the blood and the gas transport and measurement characteristics of the measurement system.

7. A method according to claim 1, wherein shape criteria of the expiratory part of the time course of the $O_2$ and $CO_2$ concentration values are used for determining the indicator.

8. A method according to claim 3, wherein shape criteria of the expiratory part of the time course of the $O_2$ and $CO_2$ concentration values are used for determining the indicator.

9. A method according to claim 1, wherein person-related basic data such as age, weight, height, sex and training state, are included in said mathematical model.

10. A method for determining an indicator which is dependent on respiratory data and defines a transition from an aerobic to an anaerobic metabolism of a person, with said person being subjected to a physical stress, wherein discrete $O_2$ and $CO_2$ concentration values are measured directly in said person's respiratory gas stream at predetermined times in the course of at least one respiration period, and wherein said indicator defining said aerobic-to-anaerobic transition is derived from said discrete $O_2$ and $CO_2$ concentration values by using a mathematical model.

11. A method according to claim 10, wherein said discrete $O_2$ and $CO_2$ concentration values are measured in a partial stream derived from said person's respiratory gas stream.

12. An apparatus for determining an indicator which depends on respiratory data from a person's respiratory gas stream and defines a transition from an aerobic to an anaerobic metabolism of a person, with said person being subjected to a physical stress, having a processor unit to process said respiratory data and an output unit, wherein sensors are provided for the measurement of the $O_2$ and $CO_2$ concentration, which sensors are positioned directly in the respiratory gas stream and are suitable to detect the time course of said $O_2$ and $CO_2$ concentration values or discrete concentration values within at least one respiration period.

13. An apparatus according to claim 12, wherein said sensors are positioned in a partial stream derived from said respiratory gas stream.

14. An apparatus according to claim 13, wherein a mask-like apparatus which rests loosely on said person's mouth and nose is provided for deriving said partial stream.

15. An apparatus according to claim 14, wherein a thermistor sensor is provided in said mask-like apparatus to determine the respiration period.

16. An apparatus according to claim 14, wherein a device for drying said respiratory gas stream is provided between said mask-like apparatus for deriving said partial stream and said sensors for measuring said $O_2$ and $CO_2$ concentrations.

17. A method for determining an indicator which is dependent on respiratory data and defines a transition from an aerobic to an anaerobic metabolism of a person, with said person being subjected to a physical stress, wherein $O_2$ and $CO_2$ concentrations are measured directly in said person's respiratory gas stream, with the time course of said $O_2$ and $CO_2$ concentration values being acquired within at least one respiration period, and wherein said indicator defining said aerobic-to-anaerobic transition is derived from shape criteria of the expiratory part of said time course of said $O_2$ and $CO_2$ concentration values using a mathematical model.

18. An apparatus for determining an indicator which depends on respiratory data from a person's respiratory gas stream and defines a transition from an aerobic to an anaerobic metabolism of a person, with said person being subjected to a physical stress, having a processor unit to process said respiratory data and an output unit, wherein sensors are provided for the measurement of the $O_2$ and $CO_2$ concentration, which sensors are positioned directly in the respiratory gas stream and are suitable to detect the time course of said $O_2$ and $CO_2$ concentration values or discrete $O_2$ and $CO_2$ concentration values within at least one respiration period, said processor unit providing an indicator derived from shape criteria of the expiratory part of said time course of said $O_2$ and $CO_2$ concentration values using a mathematical model.

* * * * *